United States Patent
Kida

(10) Patent No.: US 11,096,961 B2
(45) Date of Patent: Aug. 24, 2021

(54) PHARMACEUTICAL COMPOSITION FOR SUPPRESSING SPINAL CORD ISCHEMIC DISORDER

(71) Applicants: SUMITOMO SEIKA CHEMICALS CO., LTD., Hyogo (JP); Kotaro Kida, Tokyo (JP)

(72) Inventor: Kotaro Kida, Tokyo (JP)

(73) Assignees: SUMITOMO SEIKA CHEMICALS CO., LTD., Hyogo (JP); Kotaro Kida, Tokyo (JP)

(*) Notice: Subject to any disclaimer, the term of this patent is extended or adjusted under 35 U.S.C. 154(b) by 0 days.

(21) Appl. No.: 16/837,802

(22) Filed: Apr. 1, 2020

(65) Prior Publication Data

US 2020/0316107 A1    Oct. 8, 2020

(30) Foreign Application Priority Data

Apr. 5, 2019    (JP) ............... JP2019-072780

(51) Int. Cl.
| | | |
|---|---|---|
| *A61K 33/00* | (2006.01) | |
| *A61P 9/10* | (2006.01) | |
| *A61P 9/00* | (2006.01) | |
| *A61K 9/00* | (2006.01) | |

(52) U.S. Cl.
CPC .............. *A61K 33/00* (2013.01); *A61K 9/007* (2013.01); *A61P 9/10* (2018.01)

(58) Field of Classification Search
CPC ........... A61P 9/10; A61P 9/007; A61K 9/0085
See application file for complete search history.

(56) References Cited

PUBLICATIONS

Y. Li, et al. "Pericytes impair capillary blood flow and motor function after chronic spinal cord injury," Nat. Med. Jun. 2017; 23(6): 733-741. (Year: 2017).*
M. Rich, P. Scheinhehg, and M. S. Belle. "Relationship between Cerebrospinal Fluid Pressure Changes and Cerebral Blood Flow," Circulation Research, vol. 1, Sep. 1953, 389-395. (Year: 1953).*
S.J. Weiss, et al. "Successful Treatment of Delayed Onset Paraplegia after Suprarenal Abdominal Aortic Aneurysm Repair," Anesthesiology, V 97, No. 2, Aug. 2002, 504-506 (Year: 2002).*
Google search_Jan. 5, 2021_carbon dioxide to prevent ischemia (Year: 2020).*
Treating late onset paraplegia—Google Search_Jan. 5, 2021 (Year: 2021).*
"Hypercapnia" effective for spinal cord ischemia injuries.—Google Search_Jan. 5, 2021 (Year: 2021).*
Hypercapnia for ischemic stroke—Google Search_Oct. 12, 2020 (Year: 2020).*
Carbon dioxide for ischemic spinal cord—Google Scholar_Oct. 12, 2020 (Year: 2020).*
Joseph S. Coselli et al., "Cerebrospinal fluid drainage reducesparaplegiaafter thoracoabdominal aortic aneurysm repair-:Results of a randomized clinical trial", Journal of Vascular Surgery,35(4), 2002, p. 631-p. 639.
Christine A. Fedorow et al., "Lumbar Cerebrospinal Fluid DrainageforThoracoabdominal Aortic Surgery: Rationale andPractical Considerations for Management", Anesth & Analgesia,111(1), 2010, p. 46-p. 58.

* cited by examiner

*Primary Examiner* — Michael P Cohen
(74) *Attorney, Agent, or Firm* — Hamre, Schumann, Mueller & Larson, P.C.

(57) ABSTRACT

To provide a gaseous pharmaceutical composition for suppressing spinal cord ischemic disorder, comprising carbon dioxide.

5 Claims, 2 Drawing Sheets

PHARMACEUTICAL COMPOSITION FOR SUPPRESSING SPINAL CORD ISCHEMIC DISORDER

CROSS-REFERENCE TO RELATED APPLICATION

This application claims the benefit of priority from Japanese Patent Application No. 2019-072780, filed on Apr. 5, 2019, the entire contents of which are incorporated herein by reference.

TECHNICAL FIELD

The present invention relates to a pharmaceutical composition for suppressing a spinal cord ischemic disorder.

BACKGROUND

The number of the operations of thoracic and thoracoabdominal aortae is increasing globally with an aging society, and is more than 10,000 a year as well in Japan. Although the perioperative mortality rate of thoracic and thoracoabdominal aorta operations tends to decrease by progress in operative techniques and perioperative period management, the postoperative paraplegia by spinal cord ischemic disorder is a serious complication which has not been solved yet.

A method for improving the blood flow by cerebrospinal fluid drainage is used against spinal cord ischemia after the operation of the thoracic and thoracoabdominal aorta. It has been reported that a certain effect of improving acute paraplegia is exhibited by treatment by cerebrospinal fluid drainage (Coselli et al., Journal of Vascular Surgery, 35(4): 631-639 (2002)).

SUMMARY

However, when cerebrospinal fluid is drained excessively, the possibility of causing complications such as intracranial hemorrhage and infectious diseases is pointed out (Fedorow C A et al., Anesth & Analgesia, 111(1): 46-58 (2010)). The detailed onset mechanism of the late-onset paraplegia which appears by the spinal cord ischemic disorder after the operation of the thoracic and thoracoabdominal aorta is still unknown, and even though all the therapies including cerebrospinal fluid drainage are used, the effect of improving late-onset paraplegia is not observed. Therefore, the establishment of a therapy which enables suppressing postoperative spinal cord ischemic disorder and suppressing the onset of late-onset paraplegia is a pressing need.

An object of the present invention is to provide a pharmaceutical composition for suppressing spinal cord ischemic disorder.

The present inventors have found that the spinal cord blood flow in an ischemic state can be improved, and especially the onset of late-onset paraplegia can be suppressed remarkably by making mice inhale carbon dioxide gas unexpectedly in a test using mouse transient spinal ischemia models.

That is, the present invention provides the following [1] to [7].

[1] A gaseous pharmaceutical composition for suppressing spinal cord ischemic disorder, comprising carbon dioxide.
[2] The pharmaceutical composition according to [1], wherein the spinal cord ischemic disorder is late-onset paraplegia.
[3] The pharmaceutical composition according to [1] or [2], wherein a carbon dioxide concentration in the pharmaceutical composition is 1% or more.
[4] The pharmaceutical composition according to any one of [1] to [3], wherein administration of the pharmaceutical composition is started before ischemia.
[5] A method for suppressing spinal cord ischemic disorder, comprising: administering a gaseous pharmaceutical composition comprising a carbon dioxide gas to a subject in need for the carbon dioxide.
[6] Use of carbon dioxide gas for producing a pharmaceutical composition for suppressing spinal cord ischemic disorder.
[7] A method for suppressing spinal cord ischemic disorder, comprising: adjusting carbon dioxide partial pressure in blood of a subject to a high value.

According to the present invention, a pharmaceutical composition for suppressing spinal cord ischemic disorder can be provided.

BRIEF DESCRIPTION OF THE DRAWINGS

FIG. 2A shows the BMSs in controls.

FIG. 2B shows the BMSs in mice which inhaled 5% carbon dioxide gas.

DETAILED DESCRIPTION

Figure 1:
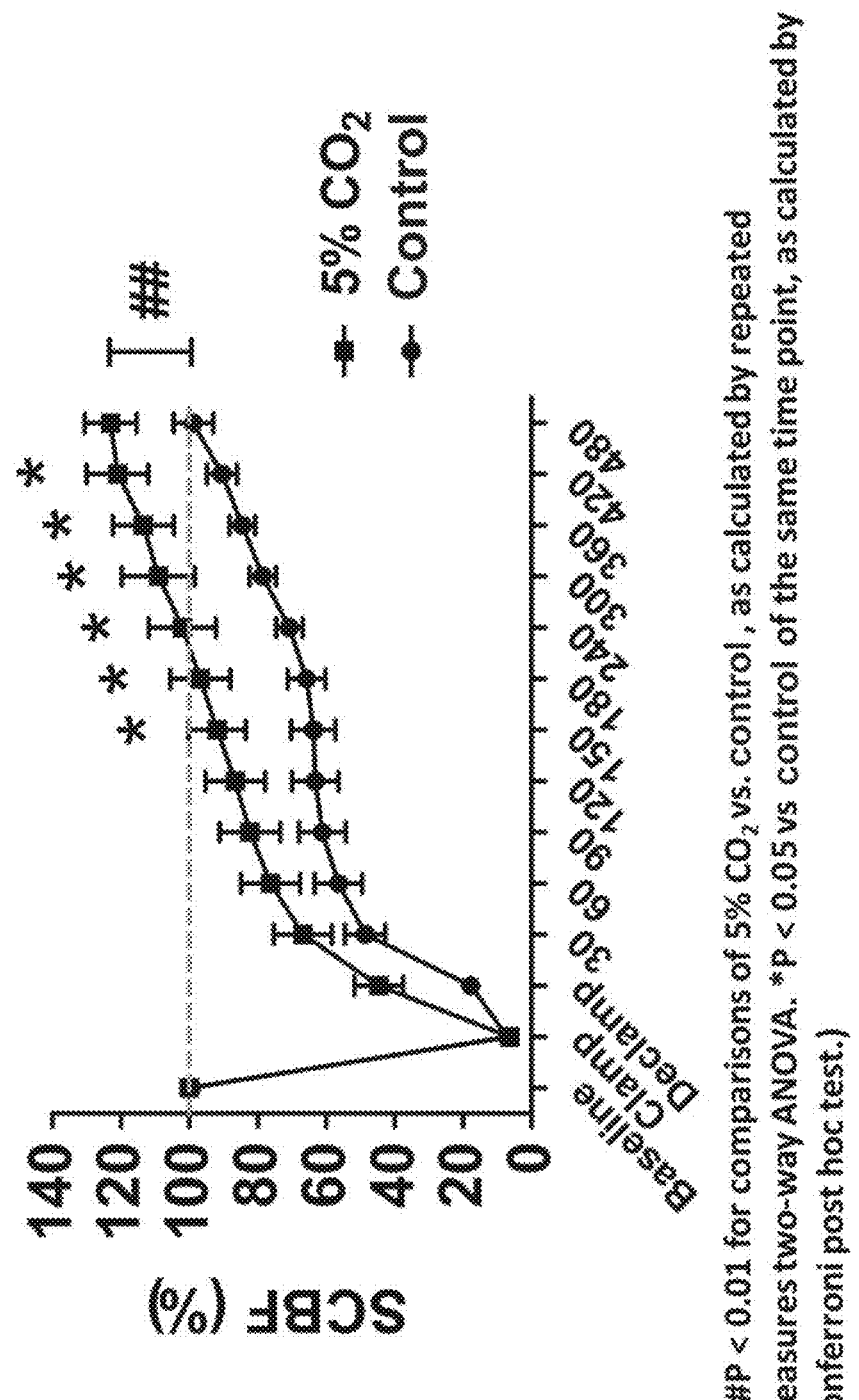
FIG. 1 is a graph showing the spinal cord blood flows (SCBFs) in mouse transient spinal cord ischemia models.

The embodiments of the present invention will be described hereinafter.

The unit of concentration "%" means "v/v %" herein.

A pharmaceutical composition according to the present embodiment is a gaseous pharmaceutical composition containing carbon dioxide gas as an active ingredient, and is a pharmaceutical composition for suppressing spinal cord ischemic disorder.

"Spinal cord ischemic disorder" means disorder which appears after ischemia in the spinal cord herein. Examples of the spinal cord ischemic disorder include late-onset paraplegia, muscle weakness, paralysis, sensory disturbance, autonomic disorder, urinary incontinence, fecal incontinence, erectile dysfunction and abnormal reflex. The present inventors have confirmed in the below-mentioned Examples that the pharmaceutical composition containing carbon dioxide gas improves the spinal cord blood flow in an ischemic state, and consider that improvement in the spinal cord blood flow contributes to the suppression of the above-mentioned disorders.

A carbon dioxide concentration in the pharmaceutical composition according to the present embodiment can be set suitably with a concentration at which the effect of suppressing spinal cord ischemic disorder can be exhibited as the lower limit value. The lower limit value of the carbon dioxide concentration can be any concentration of 1 to 20%, for example, 1%, 3%, 5%, 7%, 10%, 15% or 20%. A carbon dioxide concentration in the pharmaceutical composition according to the present embodiment at which the side effects of carbon dioxide do not appear can be set suitably as the upper limit value. The upper limit value of the carbon dioxide concentration can be, for example, 20%, 15% or 10%. Therefore, the carbon dioxide concentration in the pharmaceutical composition according to the present embodiment can be set in a range in combination of the above-mentioned lower limit value and upper limit value.

The pharmaceutical composition according to the present embodiment may further contain gas other than carbon dioxide gas such as oxygen gas, inert gases (for example, nitrogen gas, argon gas, neon gas, helium gas), hydrogen gas, nitric oxide and air. The gas other than the carbon dioxide gas contained in the pharmaceutical composition according to the present embodiment may be one type or a plurality of types. Gas other than carbon dioxide gas may be in the form of a mixed gas beforehand mixed with carbon dioxide gas, or may be mixed with carbon dioxide gas directly before or at the time of administration.

In one embodiment, the pharmaceutical composition according to the present embodiment contains carbon dioxide gas and oxygen gas. In this case, the oxygen concentration in the pharmaceutical composition can be, for example, 21% to 99%, 21% to 90%, 21% to 85%, or 21% to 80%.

In one embodiment of the present invention, the pharmaceutical composition according to the present embodiment is provided in a form which can be administered to a subject as it is. The pharmaceutical composition according to the present embodiment is specifically provided in the form of carbon dioxide gas itself or in the form of a mixed gas in which carbon dioxide gas and gas other than carbon dioxide gas such as oxygen gas are mixed.

In another aspect, the pharmaceutical composition according to the present embodiment is provided in a form prepared directly before or at the time of administration to a subject. Specifically, a container storing carbon dioxide gas and, if needed, a container storing gas other than carbon dioxide gas such as oxygen gas are connected with inhalation means (anesthetic machine or the like) through piping, and the pharmaceutical composition according to the present embodiment is provided by adjusting the flow rate and supplying the gas to the inhalation means so that carbon dioxide gas and, if needed, gas other than carbon dioxide such as oxygen gas are at suitable concentrations. Examples of the containers storing gases include gas cylinders. Gas may be stored in a container in the form of compressed gas or in the form of liquefied gas.

In another aspect, the pharmaceutical composition according to the present embodiment is provided by supplying carbon dioxide gas to an airtight space in which a subject exists. Specifically, the pharmaceutical composition according to the present embodiment is provided by adjusting the flow rate and supplying carbon dioxide gas and, if needed, gas other than carbon dioxide such as oxygen gas to the airtight space in which the subject exists so that the carbon dioxide concentration in the space is suitable.

The administration of the pharmaceutical composition concerning the present embodiment can be started at any point before ischemia, during ischemia, after ischemia until ischemic reperfusion, during ischemic reperfusion or after ischemic reperfusion in the operation of the thoracic and thoracoabdominal aorta. Especially, since the effect of suppressing spinal cord ischemic disorder can be exhibited more remarkably, it is preferable to start the administration before ischemia.

The number of the administration of the pharmaceutical composition according to the present embodiment is not particularly limited, and a single administration or a plurality of administrations can be performed depending on the severity, the sex, the age and the like of a patient.

The administration time per one administration of the pharmaceutical composition according to the present embodiment (time from the start of the administration to the end of the administration) is not particularly limited as long as the administration time is a time during which the effect of suppressing spinal cord ischemic disorder can be exhibited, and the administration time can be suitably set depending on the severity, the age, the sex and the like of a patient. The administration time per one administration may be, for example, 5 minutes to 24 hours, 10 minutes to 12 hours, 20 minutes to 6 hours, or 30 minutes to 3 hours.

Although a subject to which the pharmaceutical composition according to the present embodiment is administered is not particularly limited, the subject is preferably a human.

According to the knowledge of the present inventors, the onset of spinal cord ischemic disorder can be remarkably suppressed by increasing the carbon dioxide partial pressure in blood in the living body ($PaCO_2$). Therefore, a method for suppressing spinal cord ischemic disorder, comprising adjusting the carbon dioxide partial pressure in blood in a subject to a high value (for example, 50 mmHg or more) is provided as one embodiment of the present invention.

As long as the lower limit value of the carbon dioxide partial pressure in blood in the present embodiment is a value wherein the effect of suppressing spinal cord ischemic disorder can be exhibited, the lower limit value is not particularly limited, and may be, for example, 50 mmHg, 55 mmHg, 60 mmHg, 65 mmHg or 70 mmHg. Carbon dioxide partial pressure in blood according to the present embodiment at which the side effects of carbon dioxide do not appear can be set suitably as the upper limit value. The upper limit value of the carbon dioxide partial pressure in blood can be, for example, 200 mmHg, 150 mmHg or 100 mmHg. Therefore, the carbon dioxide concentration in the pharmaceutical composition according to the present embodiment can be set in a range in combination of the above-mentioned lower limit value and upper limit value. The carbon dioxide partial pressure in blood can be adjusted by administering (inhaling) carbon dioxide gas to the subject and reducing the respiratory rate of the subject, or the like. The carbon dioxide partial pressure in blood can be measured with an analyzer for gas in blood.

EXAMPLES

Although the present invention will be described in detail hereinafter by giving the Examples, the present invention is not limited to these Examples.

(1) Creation of Mouse Transient Spinal Cord Ischemia Model

An 8 to 12-week-old male mouse was used for creating a mouse transient spinal cord ischemia model. The mouse was subjected to endotracheal intubation under anesthesia by the inhalation of isoflurane and cannulation for measuring blood pressure in the left femoral artery. The cervix and a part of the sternum were incised, and the left common carotid artery, the aortic arch, and the left subclavian artery were exposed. The blood flow was intercepted at the aortic arch and the left subclavian artery base using two vascular clips. The vascular clips were removed 4 minutes and 30 seconds after the blood flow interception, and the blood flow interception was released. The cannula indwelling in the left femoral artery was removed 10 minutes after the release of the interception, and the wound was sutured to create a mouse transient spinal cord ischemia model.

(2) Measurement of Spinal Cord Blood Flow and Evaluation of Motor Function

Figure 2A:
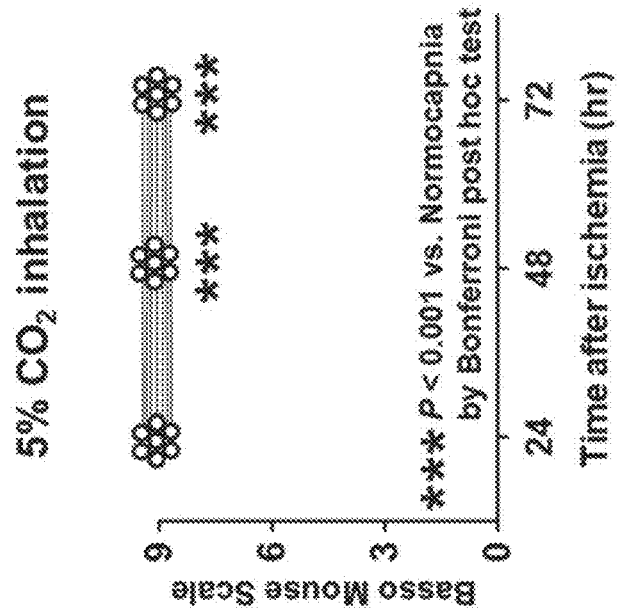
FIGS. 2A-2B are graphs showing the Basso Mouse Scales (BMSs) in mouse transient spinal cord ischemia models.
Figure 2B:
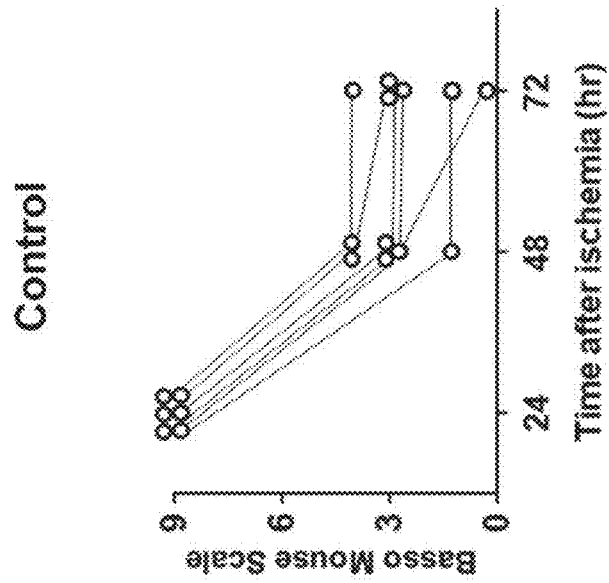

The inhalation of 5% carbon dioxide gas was started from the cannulation in the process of creating the mouse transient spine ischemia model, and the inhalation was continued until the end of the model creation. The carbon dioxide partial pressure in blood of the mouse which inhaled carbon dioxide gas was around 60 mmHg. The spinal cord blood flow (SCBF) before the blood flow interception was defined as 100%, and the spinal cord blood flow was measured for 480 seconds after the blood flow interception was released. The results are shown in FIG. 1. A known method (Basso et al., J Nurotrauma, 23(5): 635-59, 2006) was partially modified, and the motor functions were continuously evaluated by the Basso Mouse Scale (BMS) 24, 48 and 72 hours after spinal cord ischemia. The results are shown in FIGS. 2A-2B. In these figures, "BMS=0 to 5" shows death or the state of being incapable of walking (namely the state of paraplegia), and "BMS=6 to 9" shows the state of being capable of walking. Mice, wherein the inhalation of 100% oxygen gas was started after the cannulation in the process of creating a mouse transient spinal cord ischemia model, and the inhalation was continued until the end of the model creation were used as controls. The carbon dioxide partial pressures in blood of the controls were around 35 mmHg.

According to FIG. 1, it was confirmed that the spinal cord blood flow in the ischemic state improved more rapidly in the mouse which had inhaled 5% carbon dioxide gas as compared with the control. According to FIGS. 2A-2B, it was confirmed that decreases in the motor functions were hardly observed, and the onset of late-onset paraplegia was suppressed remarkably in the mice which had inhaled 5% carbon dioxide gas as compared with the controls. That is, it was confirmed that the pharmaceutical composition containing carbon dioxide gas suppressed spinal cord ischemic disorder.

What is claimed is:

1. A method for suppressing spinal cord ischemic disorder, comprising: administering a gaseous pharmaceutical composition comprising a carbon dioxide gas to a subject susceptible to developing the spinal cord ischemic disorder before manifestation of the spinal cord ischemic disorder.

2. The method according to claim 1, wherein the spinal cord ischemic disorder is late-onset paraplegia.

3. The method according to claim 1, wherein a carbon dioxide concentration in the pharmaceutical composition is 1% or more.

4. The method according to claim 1, wherein administration of the pharmaceutical composition is started before ischemia.

5. A method for suppressing spinal cord ischemic disorder, comprising: adjusting carbon dioxide partial pressure in blood of a subject susceptible to developing spinal cord ischemic disorder to a high value before manifestation of the spinal cord ischemic disorder.

* * * * *